United States Patent [19]
Davidson

[11] Patent Number: 5,258,022
[45] Date of Patent: Nov. 2, 1993

[54] ZIRCONIUM OXIDE AND NITRIDE COATED CARDIOVASCULAR IMPLANTS

[75] Inventor: James A. Davidson, Germantown, Tenn.

[73] Assignee: Smith & Nephew Richards, Inc., Memphis, Tenn.

[21] Appl. No.: 830,720

[22] Filed: Feb. 4, 1992

Related U.S. Application Data

[63] Continuation-in-part of Ser. No. 557,173, Jul. 23, 1990, Pat. No. 5,152,794, which is a continuation-in-part of Ser. No. 385,285, Jul. 25, 1989, Pat. No. 5,037,438.

[51] Int. Cl.$^5$ .......................... A61F 2/24; A61F 2/02; A01N 1/02
[52] U.S. Cl. .......................................... 623/2; 623/11; 623/900; 427/2
[58] Field of Search .................. 623/2, 900, 11; 427/2

[56] References Cited

U.S. PATENT DOCUMENTS

| | | | |
|---|---|---|---|
| 2,987,352 | 6/1961 | Watson et al. | |
| 3,643,658 | 2/1972 | Steinemenan | 128/92 D |
| 3,677,795 | 7/1972 | Bokros et al. | 623/1 |
| 3,685,059 | 8/1972 | Bokros et al. | 623/2 |
| 3,969,130 | 7/1976 | Bokros | 623/2 X |
| 4,040,129 | 8/1977 | Steinemann et al. | 3/1.9 |
| 4,145,764 | 3/1979 | Suzuki et al. | 3/1.9 |
| 4,159,358 | 6/1979 | Hench et al. | 427/319 |
| 4,223,412 | 9/1980 | Aoyagi et al. | 3/1.9 |
| 4,495,664 | 1/1985 | Blanquaert | 3/1.9 |
| 4,608,051 | 8/1986 | Reck et al. | 623/10 |
| 4,617,024 | 10/1986 | Broemer et al. | 623/10 |
| 4,652,459 | 3/1987 | Engelhardt | 427/2 |
| 4,652,534 | 3/1987 | Kasuga | 501/5 |
| 4,671,824 | 6/1987 | Haygarth | 148/6.11 |
| 4,687,487 | 8/1987 | Hintermann | 623/18 |
| 4,714,474 | 12/1987 | Brooks, Jr. et al. | 623/20 |
| 4,728,488 | 3/1988 | Gillett et al. | 376/327 |
| 4,778,461 | 10/1988 | Pietsch et al. | 623/2 |
| 4,822,355 | 4/1989 | Bhuvaneshwar | 623/2 |
| 4,834,756 | 5/1989 | Kenna | 623/16 |
| 4,955,911 | 9/1990 | Frey et al. | 623/16 |
| 5,037,438 | 8/1991 | Davidson | 623/18 |
| 5,061,278 | 10/1991 | Bicer | 623/2 |

FOREIGN PATENT DOCUMENTS

| | | |
|---|---|---|
| 770080 | 10/1967 | Canada. |
| 1140215 | 1/1983 | Canada. |
| 38902 | 11/1981 | European Pat. Off. |
| 0159410 | 12/1984 | European Pat. Off. |
| 0410711A1 | 7/1990 | European Pat. Off. |
| 1943801 | 4/1970 | Fed. Rep. of Germany. |
| 2811603 | 3/1978 | Fed. Rep. of Germany. |
| 1325269 | 8/1973 | United Kingdom. |
| 2206182A | 5/1987 | United Kingdom. |

OTHER PUBLICATIONS

Baruah Bileaflet Mechanical Cardiac Valve Prosthesis, "Instructions for Use" brochure (author and date unknown).

Pamphlet, "Zircadyne Corrosion Properties," Teledyne Wah Chang Albany (no date) pp. 1-16.

Conte, Borello and Cabrini, "Anodic Oxidation of Zircaloy-2," Jnl. of Applied Electrochemistry, vol. 6, pp. 293-299 (1976).

Haygarth and Fenwick, "Improved Wear Resistance of Zirconium by Enhanced Oxide Films," Thin Solid Films, Metallurgical and Protective Coatings, vol. 118, pp. 351-362 (1984).

"The Cementless Fixation of Hip Endoprostheses," edited by Morscher, Mittelmeier, 'Total Hip Replacement with the Autophor Cement-Free Ceramic Prosthesis,' pp. 225-241 (1984).

(List continued on next page.)

Primary Examiner—Randall L. Green
Assistant Examiner—Dinh X. Nguyen
Attorney, Agent, or Firm—Pravel, Hewitt, Kimball & Krieger

[57] ABSTRACT

The invention provides synthetic metallic heart valves fabricated of zirconium or zirconium alloys that are coated with blue-black zirconium oxide or zirconium nitride to provide a surface that is hard, biocompatible, resistant to impact, cavitation, and microfretting wear and exhibits improved hemocompatibility.

9 Claims, 1 Drawing Sheet

OTHER PUBLICATIONS

Brown and Merritt, "Evaluation of Corrosion Resistance of Bioloy," Dept. of Biomedical Engineering, Case Western Reserve University, Feb. 13, 1986 (1:8).

Davidson, Schwartz, Lynch, and Gir, "Wear, Creep and Frictional Heating of Femoral Implant Articulating Surfaces and the Effect on Long-Term Performance—Part II, Friction, Heating, and Torque," Jnl. of Biomedical Materials Research: Applied Biomaterials, vol. 22, No. A1, pp. 69-198.

ASTM F86-84, "Standard Practice for Surface Preparation and Marking of Metallic Surgical Implants," pp. 12-14 (1984), corrected editorially in May, 1987.

Khruschov, "Principles of Abrasive Wear" Wear, 28, 69-88 (1974).

Weightman and Light, "The Effect of the Surface Finish of Alumina and Stainless Steel on the Wear Rate of UHMW Polyethylene" Biomaterials, 7, 20-24 (1986).

Viegas, et al., "Metal Materials Biodegration: A Chronoamperometric Study", Journal of Materials Science: Materials in Medicine 1, 105-109, (1990).

Briscoe, et al., "The Friction and Wear of High Density Polythene: The Action of Lead Oxide and Copper Oxide Fillers" Wear, 27, 19-34 (1974).

Rabinowicz, "Lubrication of Metal Surface by Oxide Films" ASLE Translations, 10, 400-407 (1967).

Mäusli, et al., "Constitution of Oxides on Titanium Alloys for Surgical Implants" Advances In Bio Materials, 8, 305 (1988).

Rokicki, "The Passive Oxide Film on Electropolished Titanium" (Feb. 1990).

Coll and Jacquot, "Surface Modification of Medical Implants and Surgical Devices Using TiN Layers" Surface and Coatings Technology 36, 867 (1988).

Bradhurst and Heuer, "The Influence of Oxide Stress on the Breakaway Oxidation of Zircaloy-2", J. of Nuclear Materials 37, 35 (1970).

Demizu, et al., "Dry Friction of Oxide Ceramics Against Metals: The Effect of Humidity", Tribology Transactions 33, 505 (1990).

K. G. Budinski, "Tribological Properties of Titanium Alloys," pp. 289-299, vol. I, *Wear of Materials*, AMSE (1991).

R. C. Bill, "Selected Fretting-Wear-Resistant Coatings for Ti-6%Al-%Alloy" Wear 106 (1985), pp. 283-301.

G. Bertrand et al., "Morphology of Oxyde Scales Formed on Titanium," vol. 21, Oxidation of Metals, Nos. 1/2 (1983), pp. 1-19.

Robert B. More, Malcolm D. Silver; "Pyrolytic Carbon Prosthetic Heart Valve Occluder Wear: In Vivo vs. In Vitro Results For The Bjork-Shiley Prosthesis;" *Journal of Applied Biomaterials*, vol. 1, pp. 267-278 (1990).

Kowbel, Witold et al., "Effect of Boron Ion Implantation on Tribological Properties of CVD $Si_3N_4$," vol. 46 Lubrication Engineering, 10 pp. 645-650.

Author Unkown, "Boric acid: A Self-replenishing solid lubricant," Tech Spotlight, Advanced Materials and Processes pp. 40-42 (Jul. 1991).

"Increase in Biocompatibility of Polymers by Treatment With Phosphatidyl Choline," Study done by Biocompatibles Ltd., UK and Wolfson Centre for Materials Technology Brunel University (Jul. 1991).

Golomb, Gershon, et al., "Prevention of bioprosthetic heart valve tissue calcification by charge modification: Effects of protamine binding by formaldehyde," vol. 25 Jnl of Biomedical Materials Research pp. 85-98 (1991).

ZIRCONIUM OXIDE AND NITRIDE COATED CARDIOVASCULAR IMPLANTS

RELATED APPLICATIONS

This application is a continuation in part of U.S. Ser. No. 07/557,173 filed Jul. 23, 1990 which is in turn a continuation in part of U.S. Ser. No. 385,285 filed Jul. 25, 1989, now issued as U.S. Pat. No. 5,037,438.

BACKGROUND OF THE INVENTION

1. Field of the Invention

This invention relates to cardiovascular implants fabricated of zirconium or zirconium alloys that are coated with a thin layer of zirconium nitride or black or blue-black zirconium oxide to provide resistance to wear and enhanced biocompatibility. More specifically, the invention is of synthetic heart valves and artificial hearts fabricated of zirconium or zirconium alloy coated with a thin layer of zirconium nitride or black or blue-black zirconium oxide to reduce wear and enhance blood biocompatibility.

2. Description of the Related Art

Cardiovascular implants have unique blood biocompatibility requirements to insure that the device is not rejected (as in the case of tissue materials for heart valves and grafts for heart transplants) or that adverse thrombogenic (clotting) or hemodynamic (blood flow) responses are avoided. For mechanical devices, properties such as the surface finish, flow characteristics, surface structure, charge, wear and mechanical integrity all play a role in the ultimate success of the device. When these implants are fabricated from natural tissue, known as bioprostheses, they can be affected by gradual calcification and the eventual stiffening and tearing of the implant. Surface charge has been shown to play a key role in the propensity of these bioprostheses to form calcium phosphate deposits Non-bioprosthetic devices (mechanical) are fabricated from materials such as pyrolytic carbon-coated graphite, pyrolytic carbon-coated titanium, stainless steel, titanium alloys, cobalt-chrome alloys, cobalt-nickel alloys, alumina coated with polypropylene and poly-4-fluoroethylene. Typical materials used for balls and disks for heart valves include nylon, silicone, hollow titanium, TEFLON TM, polyacetal, graphite, and pyrolytic carbon. Artificial hearts are fabricated from various combinations of titanium, carbon fiber reinforced composites, polyurethanes, BIDLON TM (DuPont), Hemothane TM (Sarns/3M), DACRON TM, polysulfone, and other thermoplastics. One of the most significant problems encountered in both heart valves and artificial hearts is the formation of blood clots. Protein coatings are sometimes employed to reduce the risk of blood clot formation.

It has been found that stagnant flow regions also contribute to the formation of blood clots. These stagnant regions can be minimized by optimizing surface smoothness and minimizing abrupt changes in the size of the cross section through which the blood flows or minimizing either flow interference aspects. While materials selection for synthetic heart valves and cardiac implants generally is therefore dictated by a requirement for blood compatibility to avoid the formation of blood clots, cardiovascular implants must also be designed to optimize blood flow and wear resistance.

Even beyond the limitations on materials imposed by the requirements of blood biocompatibility and limitations to designs imposed by the need to optimize blood flow, there is a need for durable designs since it is highly desirable to avoid the risk of a second surgical procedure to implant cardiovascular devices. Further, a catastrophic failure of the device will almost certainly result in the death of the patient.

The most popular current heart valve designs include the St. Jude medical tilting disk double cusp (bi-leaf) valve. This valve includes a circular ring-like pyrolytic carbon valve housing or frame and a flow control element which includes pyrolytic carbon half-disks or leaves that pivot inside the housing to open and close the valve. The two leaves have a low profile and open to 85° from the horizontal axis.

Another popular heart valve is the Medtronic-Hall Valve wherein the flow control element is a single tilting disk made of carbon coated with pyrolytic carbon which pivots over a central strut inside a solid titanium ring-like housing. A third, less popular design, is the Omniscience valve which has a single pyrolytic disk as a flow control element inside a titanium housing. Finally, the Starr-Edwards ball and cage valves have a silastic ball riding inside a cobalt-chrome alloy cage. The cage is affixed to one side of a ring-like body for attachment to the heart tissue.

The St. Jude and Medtronic-Hall valves appear to be best suited to maximize hemodynamic performance from a design standpoint. However from the point of view of durability, these heart valves could fail from disk fracture related to uneven pyrolytic carbon coating, fracture of the ball cage, disk impingement, strut wear, disk wear, hinge failure, and weld failure.

A more recent heart valve, the Baruah Bileaflet is similar to the St. Jude design but opens to 80° and is made of pure zirconium. The valve has worked well over its approximately two year history with roughly 200 implants to date in India. This performance can be partly attributed to the lower elastic modulus of zirconium (about 90 GPa) and the resultant lower contact stress severity factory (Cc of about $0.28 \times 10^{-7}$ m) when the disk contacts the frame. In contrast, pyrolytic constructions produce contact stress severity factors of about $0.54 \times 10^{-7}$ m.

Although zirconium has worked well to date and can reduce contact stress severity, zirconium metal is relatively soft and sensitive to fretting wear. This is partly due to the hard, loosely attached, naturally-present passive oxide surface films (several nanometers in thickness) which can initiate microabrasion and wear of the softer underlying metal. However, this naturally present zirconium oxide passive film is thrombogenically compatible with blood and the design is acceptable from a hemodynamic standpoint. Therefore, while the zirconium bileaflet valve appears to meet at least two of the major requirements for cardiac valve implants, namely blood compatibility and design for minimum stagnant flow regions, the use of soft zirconium metal leads to a relatively high rate of fretting wear and leads to the expectation that the valve may be less durable than one produced from materials less susceptible to fretting wear.

There exists a need for a metallic cardiac valve implant that is biocompatible, compatible with blood in that it does not induce blood clotting and does not form a calcified scale, that is designed to minimize stagnant flow areas where blood clotting can be initiated, that has a low elastic modulus for lower contact stress severity factors to ensure resistance to wear from impact and that has a surface that is also resistant to microabrasion thereby enhancing durability.

SUMMARY OF THE INVENTION

The invention zirconium or zirconium alloy heart valves coated with a thin layer of blue-black or black zirconium oxide or zirconium nitride provides heart valves that are biocompatible, compatible with blood, have low modulus of elasticity for lowered contact stress severity, and are also resistant to cavitation, microfretting and impact-induced wear due to their hard oxide or nitride surface. The thin surface coatings are formed in situ by oxidation or nitridation of the surface of a zirconium or zirconium alloy heart valve to form a continuum with the underlying metal so that there is no sharp line of demarcation between the metallic substrate and the coating, as may be found when other coating processes that involve application overlay coating techniques of various oxides or nitrides onto a variety of metal substrates.

The in situ surface-hardened oxide or nitride coatings of zirconium or zirconium alloys may be highly polished to a mirror finish to further improve blood flow characteristics of the valve. Furthermore, the oxide- or nitride-coated surfaces may be coated with substances to further enhance biocompatibility and performance. For example, phosphatidyl choline for reducing platelet adhesion to the surfaces of the valve, or boranated or silver-doped hardened surface layers to reduce friction and wear between contacting parts of heart valves, prosthetic artificial hearts, and other cardiovascular implants.

The thickness of the hard surface layer is preferably less than about 5 microns for optimal residual compressive stresses and minimal dimensional changes or distortion during oxidation or nitridation. Unlike solid pyrolytic carbon constructs, the zirconium or nitride surface layers on the metal substrate greatly improve the strength and ductility of the heart valve or other cardiovascular implants. Furthermore, the in situ type of hardening process provides a relatively uniform hard surface layer on all parts of the surface, including inside diameters and corners, unlike the line of sight type processes used to apply pyrolytic carbon or other ceramic-type overlay coatings, such as physical or chemical vapor deposition or ion implantation.

The inherently lower modulus of zirconium and zirconium alloys (about 13 million psi) provide a more flexible and forgiving construct for cardiovascular applications and improve contact stress levels, valve closure, and the ability of the valve leaves to self-align with blood to reduce thrombodynamic effects. While zirconium metal itself may be used, its alloys are also useful and are in many applications to be preferred. These alloys include all those zirconium alloys, which when subjected to an oxidizing or nitriding atmosphere, will produce a tightly adherent hard oxide or nitride coating that is less than about 5 microns thick. It is understood that when a zirconium alloy is used the oxide or nitride coating will also contain, to varying degrees, oxides or nitrides of the alloying constituents. In the specification and claims, such coatings are intended to fall within the definition of in situ formed zirconium oxide or zirconium nitride surface coatings.

Given the biocompatibility and blood compatibility of zirconium oxide and zirconium nitride coatings, it is expected that these materials will find use in other cardiovascular applications. For example, surface hardened zirconium wire may be braided into useful form for vascular grafts. Further, the metallic, carbon, and polymeric mechanical parts of artificial hearts such as heart pumps, valves, etc. may be fabricated of zirconium or zirconium alloys which may be then be coated via in situ oxidation or nitriding to form a blue-black or black oxide of zirconium or zirconium nitride, respectively.

DETAILED DESCRIPTION OF THE PREFERRED EMBODIMENT

The invention provides zirconium or zirconium alloy heart valves that are coated with a thin layer of blue-black or black zirconium oxide or zirconium nitride. These valves, with their hardened surfaces, are biocompatible, hemo-compatible, and have a low modulus of elasticity for reduced contact stress severity. Furthermore, the hardened surfaces of these valves are more resistant to microfretting and impact-induced wear than the underlying softer zirconium or zirconium alloy metal substrates. Therefore, the heart valves offer a significant improvement in terms of biocompatibility and longevity. In addition, the hardened oxide or nitride surfaces may be further modified with, for example, phosphatidyl choline for reducing platelet adhesion or by boranation or silver doping of the surface to further improve friction and wear characteristics between connecting moving parts.

Figure 1:
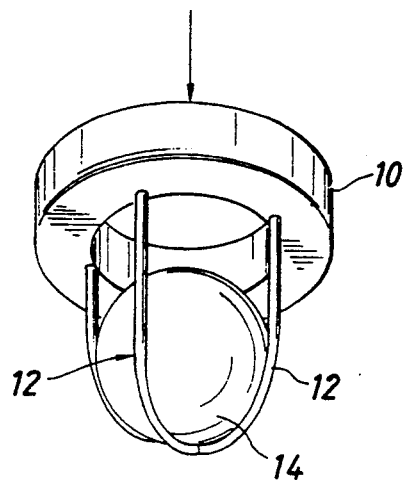
FIG. 1 shows a simplified representation of a ball valve like the Starr-Edwards valve.

In its simplest form, a synthetic cardiac valve includes a valve body for affixing the valve to the body tissue and through which blood flows, and a flow control element for allowing or blocking off blood flow. For instance, FIG. 1 shows a typical ball valve having a valve body that includes a ring-like housing 10 and valve struts 12. A flow control element, in this instance a ball 14, fits within the cage formed by the struts 12. The valve allows flow of blood in only one direction, from top to bottom as shown in FIG. 1. When flow is reversed, the ball is lifted upwards, contacts the interior perimeter of the ring-like housing 10, and blocks off the space within the ring through which blood flows. Thus, during normal operation, the ball moves upward and downward thereby impacting both the interior periphery of the ring-like housing 10 and also the struts 12. Consequently, it may be expected that signs of wear due to impact would appear at the struts and inner portion of the ring-like housing at those points where the ball contacts these elements in normal use. Invention heart valves of this type of construction would have the ring-like housing 1 and the struts 12 fabricated of zirconium or zirconium alloy. These components would then be oxidized or nitrided, as explained below, to produce a thin surface coating, not more than about 5 microns thick of blue-black or black zirconium oxide or zirconium nitride on the surface. When the ball then performs its normal flow control function, during which it impacts the struts and inner periphery of the housing 10, it would encounter a hardened surface with a low elastic modulus underlying metal substrate. As a result of oxidizing or nitriding the surfaces for hardening, impact wear would be significantly reduced. Further, since the modulus of elasticity of zirconium is about 90 Gpa, the resultant contact stress severity factor would be about $0.28 \times 10^{-7}$ m. This is in sharp contrast to pyrolytic constructs which have contact stress severity factors of about $0.54 \times 10^{-7}$ m.

Figure 2:
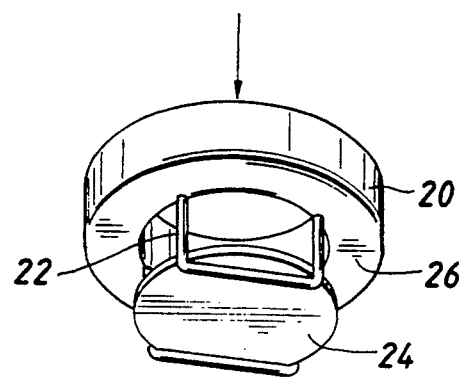
FIG. 2 is a simplified representation of a disc valve.

FIG. 2 shows a disc-type valve, where the valve body includes a ring-like housing 20 to which is attached struts 22 which form a cage on one side of the valve. A flow control element, in this case a disc 24, is held in place in the cage formed by the struts 22. The valve is shown in the open position so that blood flows from the top to the bottom of the figure. When blood flow is reversed, the disc moves upward and contacts the lower face 26 of the ring structure 20 blocking off the aperture in the ring thereby preventing blood flow. Therefore, in normal operation, the disc will move upwards and downwards alternately contacting the cage formed by the struts and the lower surface of the ring structure 26. It may be expected that impact induced wear would commence at the points where the disc contacts the struts and the ring 26. In the invention valve, the struts 22 and ring 20 would be fabricated from zirconium or zirconium alloy having a low modulus of elasticity. These components would then be oxidized or nitrided to produce a surface coating less than about 5 microns thick, as described below. Optionally, the disc 24 may also be fabricated from zirconium or zirconium alloy and may also be surface oxidized or nitrided. These hardened oxidized or nitrided surfaces, when they are brought into contact in normal use, will suffer reduced impact-induced, cavitation, or fretting wear.

Figure 3:
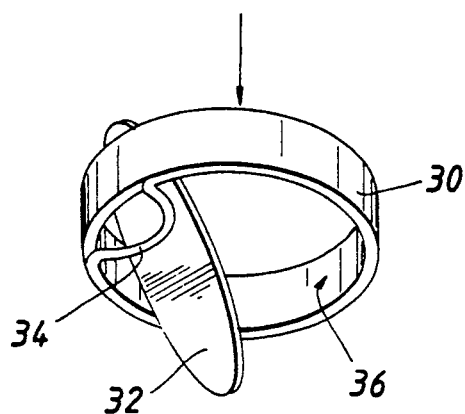
FIG. 3 is a simplified representation of a tilting disc, single cusp valve like the Medtronic-Hall valve.

FIG. 3 shows a tilting disc, single cusp valve of the Medtronic-Hall type. This valve has a valve body including a ring-like housing 30 to which is affixed a strut 34 for controlling disc motion. The disc 32 is affixed to the housing 30 with hinge elements attached to the disc (leaflet). The flow control element of this valve is a single-cusp disc 32 which is able to tilt about the hinge and limited by strut 34 to open and close the opening in ring-like housing 30. The valve in FIG. 3 is shown in the open position with blood flowing from the top to the bottom of the figure. When flow is reversed, the disc 32 tilts upward and closes the aperture in the ring-like housing 30. The strut 34 is welded to the housing 30 and is subject to significant forces as the disc 32 moves to open and close the aperture in the valve. Similarly, the disc hinge element also experiences significant force. Consequently, it may be expected that the welded part of the strut or the hinge could fail. Further, the disc itself impacts the inside surface 38 of the ring-like housing 30 upon closing. Therefore, wear might be expected at the periphery of the disc and on the interior surface 36 of the housing 30. The invention tilting disc single-cusp valve is fabricated of zirconium or zirconium alloy metal that is subjected to a surface oxidation or nitridation process, as described below, to provide a surface coating of less than about 5 microns thick. Because of the low modulus of elasticity of the zirconium-type metals used, the life cycle of the welded strut 34 may be expected to increase. Further, the hardened oxide or nitride coatings provide a surface less susceptible to impact, cavitation, or fretting wear so that both the hinges and fit between the disc 32 and inside surface 36 of the ring-like housing 30 may be expected to remain integral for a longer period of time. Therefore, the invention provides for a significant improvement in the longevity and efficiency of the Medtronic-Hall type valves.

Figure 4:
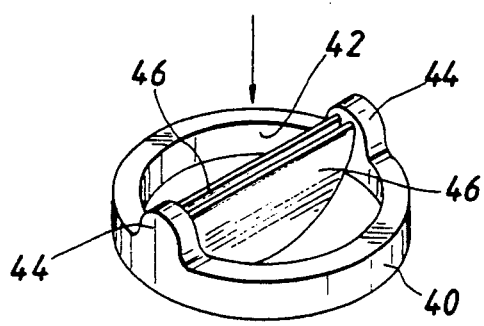
FIG. 4 is a simplified representation of a tilting disc, double cusp or bi-leaflet valve of the St. Jude or Baruah-type.

FIG. 4 shows a St. Jude or Baruah-type valve having a valve body including an outer ring-like housing 40 with an inner ring 42 that has two flanges 44 each containing two slots for receiving hinges attached to leaflets. The flow control element of this valve comprises two leaflets 46, in the approximate shape of half discs, with hinge elements attached at diametrically opposite ends. These hinge elements fit within the apertures or slots in the flanges 44 of the inner ring 42 and are able to rotate through less than 180° in these apertures. Thus, in operation, the flow control elements are in the position shown in FIG. 4 with the valve open with blood flowing from top to bottom. When blood flow reverses and flows from bottom to top, the bi-leaflets 46 pivot about their hinges to close the apertures in the ring-like valve body. Consequently, there is a significant amount of movement about the hinge elements and slots where microfretting wear might be initiated. Furthermore, the bi-leaflet half disc flow control elements 46 may impinge upon the inner ring 42 of the valve body, thereby leading to cavitation or impact-induced wear. Invention valves of the St. Jude or Baruah-type have the same construction but are fabricated of zirconium or zirconium alloys. These valves are coated with a hard outer surface coating of blue-black or black zirconium oxide or zirconium nitride that is resistant to microfretting wear at the hinge points and impact wear at those locations where the flow control element impacts the valve body. Consequently, it might be expected that the invention valve would have a longer cycle life than the currently used St. Jude or Baruah valves. Indeed, as mentioned before, the Baruah valve is currently fabricated of zirconium or zirconium alloys and would therefore be subject to relatively rapid wear because of the relative softness of zirconium and its alloys, when used without the invention oxide or nitride coatings.

In order to form continuous and useful zirconium oxide or nitride coatings over the desired surface of the metal alloy prosthesis substrate, the metal alloy should contain from about 80 to about 10 wt. % zirconium, preferably from about 95 to about 100 wt. %. Niobium, tantalum, and titanium include common alloying elements in the alloy with often times the presence of hafnium. Yttrium may also be alloyed with the zirconium to enhance the formation of a tougher, yttria-stabilized zirconium oxide coating during the oxidation of the alloy. While such zirconium and zirconium alloys may be custom formulated by conventional methods known in the art of metallurgy, a number of suitable alloys are commercially available. These commercial alloys include among others Zircadyne 705, Zircadyne 702, and Zircalloy.

The base zirconium containing metal alloys are cast or machined from wrought metal stock by conventional methods to the shape and size desired to obtain a prosthesis substrate. The substrate is then subjected to process conditions which cause the natural (in situ) formation of a tightly adhered, diffusion-bonded coating of zirconium oxide on its surface. The process conditions include, for instance, air, steam, or water oxidation or oxidation in a fluidized or salt bath. These processes ideally provide a thin, hard, dense, blue-black or black, low-friction wear-resistant zirconium oxide film or coating of thicknesses typically less than several microns ($10^{-6}$ meters) on the surface of the prosthesis substrate. Below this coating, diffused oxygen from the oxidation process increases the hardness and strength of the underlying substrate metal.

Unlike the prior art titanium oxides of, for example, Steinemenan's U.S. Pat. No. 3,643,658, the oxygen supplied to form the blue-black or black zirconium oxide coatings of the invention is a beneficial alloying component which improves the immediate substrate metal hardness which improves oxide attachment strength and durability and also improves the base-metal strength. Thus, the fatigue strength of the underlying zirconium metal is improved thereby increasing the potential life of the prosthesis. In contrast, oxygen in titanium alloys tends to stabilize the lower strength α-phase which significantly reduces the metal's fatigue strength.

The air, steam and water oxidation processes are described in now-expired Watson U.S. Pat. No. 2,987,352, the teachings of which are incorporated by reference as though fully set forth. The air oxidation process provides a firmly adherent black or blue-black layer of zirconium oxide ($ZrO_2$) of highly oriented monoclinic crystalline form. If the oxidation process is continued to excess, the coating will whiten and separate from the metal substrate. The oxidation step may be conducted in either air, steam or hot water. For convenience, the metal prosthesis substrate may be placed in a furnace having an oxygen-containing atmosphere (such as air) and typically heated at 700°–1100° F. up to about 6 hours. However, other combinations of temperature and time are possible. When higher temperatures are employed, the oxidation time should be reduced to avoid the formation of the white oxide.

It is preferred that a blue-black zirconium oxide layer ranging in thickness from about 1 to about 5 microns should be formed. For example, furnace air oxidation at 1000° F. for 3 hours will form an oxide coating on Zircadyne 705 about 3–4 microns thick. Longer oxidation times and higher oxidation temperatures will increase this thickness, but may compromise coating integrity. For example, one hour at 1300° F. will form an oxide coating about 14 microns in thickness, while 21 hours at 1000° F. will form an oxide coating thickness of about 9 microns. Of course, because only a thin oxide is necessary on the surface, only very small dimensional changes, typically less than 10 microns over the thickness of the prosthesis, will result. In general, thinner coatings (1–4 microns) have better attachment strength, and more favorable residual surface stresses The thickness of the blue-black or black zirconium oxide coatings on the invention prostheses provides a further distinction between the invention and the titanium oxide coatings of Steinemann U.S. Pat. No. 3,643,658. Titanium oxide films, whether prepared by high temperature (350° C.) oxidation or high current density anodizing, are thin, powdery and loosely adherent. This is because various forms of titanium oxide form as the oxide thickens. Consequently, these films can be more easily removed under fretting conditions in vivo exposing metal surface to bodily fluids with resulting metal ion release into the body tissue. The thicker, crystalline, more tightly adherent blue-black or black zirconium oxide films, by contrast, do not readily spall or separate from the alloy substrate and form essentially only one type of $ZrO_2$ oxide as compared to the multiple oxides for Ti. It is speculated that the diffusion of oxygen into the underlying zirconium alloy provides a natural interlayer to which the zirconium oxide can adhere readily and tightly. Consequently, these zirconium oxide coatings provide excellent protection against corrosion by bodily fluids.

One of the salt-bath methods that may be used to apply the zirconium oxide coatings to the metal alloy prosthesis, is the method of Haygarth U.S. Pat. No. 4,671,824, the teachings of which are incorporated by reference as though fully set forth. The salt-bath method provides a similar, slightly more abrasion resistant blue-black or black zirconium oxide coating. The method requires the presence of an oxidation compound capable of oxidizing zirconium in a molten salt bath. The molten salts include chlorides, nitrates, cyanides, and the like. The oxidation compound, sodium carbonate, is present in small quantities, up to about 5 wt. %. The addition of sodium carbonate lowers the melting point of the salt. As in air oxidation, the rate of oxidation is proportional to the temperature of the molten salt bath and the '824 patent prefers the range 550°–800° C. (1022°–1470° C.). However, the lower oxygen levels in the bath produce thinner coatings than for furnace air oxidation at the same time and temperature. A salt bath treatment at 1290° F. for four hours produces an oxide coating thickness of roughly 7 microns. Residual contaminants in the salt bath may be inadvertently left on the treated implant surface and produce adverse clinical results. While some of these may be removed by polishing and washing, it is nonetheless preferred to use the gas (air) oxidation/nitridation processes which provides less possibility of contamination by other elements.

Whether air oxidation in a furnace, in a fluidized bed, or salt bath oxidation is used, the zirconium oxide coatings are quite similar in hardness. For example, if the surface of a wrought Zircadyne 705 (Zr, 2–3 wt. % Nb) prosthesis substrate is oxidized, the hardness of the surface shows a dramatic increase over the 200 Knoop hardness of the original metal surface. The surface hardness of the blue-black zirconium oxide surface following oxidation by either the salt bath or air oxidation process is approximately 1700–2000 Knoop hardness.

In situ air oxidation is the preferred method for producing the invention oxide coatings because it minimizes the potential for surface contamination, and allows oxygen diffusion into the metal substrate thereby allowing the formation of a tightly adherent oxide coating while also strengthening the zirconium metal.

While the above discussion has dealt mainly with blue-black or black zirconium oxide coatings on prostheses, zirconium nitride coatings are also effective in reducing wear on opposing surfaces and preventing corrosion of the underlying substrate by bodily fluids.

Even though air contains about four times as much nitrogen as oxygen, when zirconium or a zirconium alloy is heated in air as described above, the oxide coating is formed in preference to the nitride coating. This is because the thermodynamic equilibrium favors oxidation over nitridation under these conditions. Thus, to form a nitride coating the equilibrium must be forced into favoring the nitride reaction. This is readily achieved by elimination of oxygen and using a nitrogen or ammonia atmosphere instead of air or oxygen when a gaseous environment (analogous to "air oxidation") is used.

In order to form a zirconium nitride coating of about 5 microns in thickness, the zirconium or zirconium alloy prosthesis should be heated to about 800° C. for about one hour in a nitrogen atmosphere. Thus, apart from the removal of oxygen (or the appropriate reduction in oxygen partial pressure), or increasing the temperature, conditions for forming the zirconium nitride coating do not differ significantly from those needed to form the blue-black or black zirconium oxide coating. Any needed adjustment would be readily apparent to one of ordinary skill in the art.

When a salt bath method is used to produce a nitride coating, then the oxygen-donor salts should be replaced with nitrogen-donor salts, such as, for instance cyanide salts. Upon such substitution, a nitride coating may be obtained under similar conditions to those needed for obtaining an oxide coating. Such modifications as are necessary, may be readily determined by those of ordinary skill in the art.

Alternatively, the zirconium oxide or nitride may be deposited onto the zirconium or zirconium alloy surface via standard physical or chemical vapor deposition methods, including those using an ion-assisted deposition method. Techniques for producing such an environment are known in the art.

Regardless of how the zirconium oxide or nitride surface layer is formed on the zirconium or zirconium alloy substrate, the friction and wear (tribiological) aspects of the surface can be further improved by employing the use of silver doping or boronation techniques. Ion-beam-assisted deposition of silver films on zirconia ($ZrO_2$) ceramic surfaces can improve tribiological behavior. The deposition of up to about 3 microns thick silver films can be performed at room temperature in a vacuum chamber equipped with an electron-beam hard silver evaporation source. A mixture of argon and oxygen gas is fed through the ion source to create an ion flux. One set of acceptable silver deposition parameters consists of an acceleration voltage of 1 kev with an ion current density of 25 microamps per $cm^2$. The silver film can be completely deposited by this ion bombardment or formed partially via bombardment while the remaining thickness is achieved by vacuum evaporation. Ion bombardment improves the attachment of the silver film to the zirconium oxide or nitride substrate. Similar deposition of silver films on existing metal cardiovascular implants may also be performed to improve tribiological behavior.

An alternate method to further improve the tribiological behavior of zirconium oxide, zirconium nitride, or other metal cardiovascular implant surfaces is to apply boronation treatments to these surfaces such as commercially available boride vapor deposition, boron ion implantation or sputter deposition using standard ion implantation and evaporation methods, or form a boron-type coating spontaneously in air. Boric Acid ($H_3BO_3$) surface films provide a self-replenishing solid lubricant which can further reduce the friction and wear of the ceramic substrate. These films form from the reaction of the $B_2O_3$ surface (deposited by various conventional methods) on the ceramic (i.e., zirconium oxide) with water in the body to form lubricious boric acid. Conventional methods that can be used to deposit either a boron (B), $H_3BO_3$, or $B_2O_3$ surface layer on the cardiovascular implant surface include vacuum evaporation (with or without ion bombardment) or simple oven curing of a thin layer over the implant surface. The self-lubricating mechanism of $H_3BO_3$ is governed by its unique layered, triclinic crystal structure which allows sheets of atoms to easily slide over each other during articulation, thus minimizing substrate wear and friction.

Although the invention has been described with reference to its preferred embodiments, those of ordinary skill in the art may, upon reading this disclosure, appreciate changes and modifications which may be made and which do not depart from the scope and spirit of the invention as described above or claimed hereafter.

I claim:

1. A heart valve prosthesis, for implantation in body tissue of a patient, the heart valve having enhanced hemocompatibility and improved resistance to wear, comprising:
   (a) a valve body fabricated from the metals selected from the group consisting of zirconium and zirconium-containing alloys for affixing the valve to the body tissue of a patient, said valve body having an aperture through which blood is able to flow;
   (b) a flow control component fabricated from the metals selected from the group consisting of zirconium and zirconium-containing alloys able to move relative to the valve body to close the aperture in the valve body thereby blocking the blood flow through the aperture;
   (c) means, attached to the valve body, for restraining said flow control component in close proximity to the aperture in the valve body; and
   (d) a blood compatible coating selected from the group of coatings consisting of zirconium nitride, blue-black zirconium oxide and black zirconium oxide, said coating formed on at least surfaces of the valve flow control component and valve body in contact with blood and subject to impinging contact and fretting wear when the valve is in use.

2. The valve of claim 1 wherein the valve body comprises a ring and the flow control component is a disk able to close the aperture in the ring thereby blocking the flow of blood.

3. The valve of claim 1 wherein the valve body comprises a ring with an aperture for blood flow and the valve flow control component comprises a bi-leaflet able to pivot about a strut mounted diametrically across the ring to block the flow of blood.

4. The valve of claim 1 wherein the valve body comprises a ring with a periphery and an aperture for blood flow, a cage is attached to the periphery of one side of said ring, and the valve flow control component is a sphere, having a diameter larger than a diameter of said aperture, said sphere movably positioned within the cage and able to block flow of blood through the aperture in the valve body when the sphere contacts the ring.

5. The valve of claim 1 wherein the valve body comprises a ring with a periphery and an aperture for blood flow, a cage is attached to the periphery of one side of said ring, and the valve flow control component is a disk, having a diameter larger than a diameter of said aperture, said disk movably positioned within the cage and able to block flow of blood through the aperture in the valve body when the disk contacts the ring.

6. The valve of claim 1 wherein surfaces of the entire valve are coated with zirconium oxide selected from the group consisting of blue-black and black zirconium oxide.

7. The valve of claim 1, wherein the coating is from about 1 to about 5 microns thick.

8. The valve of claim 7, wherein the coating is blue black or black zirconium oxide formed by a process of in situ oxidation.

9. The valve of claim 7, wherein the coating is zirconium nitride formed by a process of in situ nitridation.

* * * * *